United States Patent
Idelevich et al.

(10) Patent No.: US 10,046,007 B2
(45) Date of Patent: Aug. 14, 2018

(54) COMPOSITIONS AND METHODS FOR TREATMENT OF SHORT TELOMERE DISORDERS

(71) Applicant: PRESCIENT PHARMA LLC, Canton, MA (US)

(72) Inventors: Pavel Idelevich, Hingham, MA (US); Yanming Wang, Southborough, MA (US)

(73) Assignee: Prescient Pharma, LLC, Canton, MA (US)

( * ) Notice: Subject to any disclaimer, the term of this patent is extended or adjusted under 35 U.S.C. 154(b) by 0 days.

(21) Appl. No.: 15/192,557

(22) Filed: Jun. 24, 2016

(65) Prior Publication Data

US 2016/0375052 A1    Dec. 29, 2016

Related U.S. Application Data

(60) Provisional application No. 62/184,029, filed on Jun. 24, 2015.

(51) Int. Cl.
| *A61K 33/00* | (2006.01) |
| *A61K 45/06* | (2006.01) |
| *A61K 38/14* | (2006.01) |
| *A61K 9/00* | (2006.01) |

(52) U.S. Cl.
CPC .............. *A61K 33/00* (2013.01); *A61K 9/007* (2013.01); *A61K 38/14* (2013.01); *A61K 45/06* (2013.01)

(58) Field of Classification Search
CPC ........ A61K 9/007; A61K 33/00; A61K 38/14; A61K 45/06; A61K 2300/00
See application file for complete search history.

(56) References Cited

U.S. PATENT DOCUMENTS

| 8,236,786 B2 | 8/2012 | Finch et al. | |
| 8,551,534 B2 | 10/2013 | Boucher et al. | |
| 8,758,824 B2 | 6/2014 | Lipp et al. | |
| 2007/0071691 A1 | 3/2007 | Brown et al. | |
| 2008/0066741 A1 | 3/2008 | LeMahieu et al. | |
| 2010/0150898 A1 | 6/2010 | Boucher, Jr. | |
| 2012/0041016 A1* | 2/2012 | Frincke | A61K 31/352 514/284 |
| 2012/0064126 A1 | 3/2012 | Sung et al. | |
| 2012/0083531 A1 | 4/2012 | Clarke et al. | |
| 2013/0028942 A1 | 1/2013 | Surber et al. | |
| 2013/0071495 A1* | 3/2013 | Koenigshoff | A61K 31/4015 424/722 |
| 2013/0266653 A1 | 10/2013 | Lipp et al. | |
| 2014/0134251 A1 | 5/2014 | Lipp et al. | |
| 2014/0336159 A1 | 11/2014 | Clarke et al. | |

FOREIGN PATENT DOCUMENTS

| WO | 2012030664 A1 | 3/2012 | |
| WO | 2012044736 A1 | 4/2012 | |
| WO | 2013130767 A1 | 9/2013 | |
| WO | WO-2014138907 A1 * | 9/2014 | ........... A61K 31/192 |

OTHER PUBLICATIONS

Alder et al., "Telomere Length Is a Determinant of Emphysema Susceptibility", 2011, American Journal of Respiratory and Critical Care Medicine, vol. 184, pp. 904-912.*
Parry et al., "Syndrome complex of bone marrow failure and pulmonary fibrosis predicts germline defects in telomerase", May 26, 2011, Blood, vol. 117, No. 21, pp. 5607-5611. (Year: 2011).*
Sun et al., "Oxidative interactions of synthetic lung epithelial lining fluid with metal-containing particulate matter." Am J Physiol Lung Cell Mol Physiol. Oct. 2001;281(4):L807-15.
Salem et al., "Nanosized rods agglomerates as a new approach for formulation of a dry powder inhaler." Int J Nanomedicine. 2011; 6: 311-320.
Sung et al., Formulation and In Vitro Characterization of Novel Dry Powder Drug Delivery Technology Respiratory, Drug Delivery Europe 2011.
Convery et al., Asthma precipitated by cessation of lithium treatment, Postgrad Med J 1999;75:637-638.
"Pulmatrix Announces Presentations at ATS 2012 International Conference Pulmatrix", pulmatrix.com, [webcite citation].
Armanios, M., "Syndromes of Telomere Shortening." Annu Rev Genomics Hum Genet. 2009 ; 10: 45. doi:10.1146/annurev-genom-082908-150046.
Martinsson et al., "Long-term lithium treatment in bipolar disorder is associated with longer leukocyte telomeres." Translational Psychiatry (2013) 3, e261; doi:10.1038/tp.2013.37; published online May 21, 2013.

* cited by examiner

*Primary Examiner* — Michael B. Pallay
(74) *Attorney, Agent, or Firm* — A. Ed Khalili; Bekiares Eliezer LLP (57) ABSTRACT

The invention generally relates to methods of treating short telomere disorders using known compounds and pharmaceutical compositions comprising same. More specifically, the disclosed methods comprise, in one aspect, the step of administering to the subject an effective amount of at least one lithium compound or a pharmaceutically acceptable salt thereof, thereby treating the subject for the short telomere disorder. This abstract is intended as a scanning tool for purposes of searching in the particular art and is not intended to be limiting of the present invention.

15 Claims, 5 Drawing Sheets

COMPOSITIONS AND METHODS FOR TREATMENT OF SHORT TELOMERE DISORDERS

CROSS REFERENCE TO RELATED APPLICATIONS

This claims the benefit of priority to U.S. Provisional Patent Application Ser. No. 62/184,029 filed Jun. 24, 2015, which is hereby incorporated herein by reference in its entirety.

FIELD OF INVENTION

This disclosure relates to compositions and methods for treating short telomere disorders.

BACKGROUND

Telomeres, the specialized nucleoproteic structures, cap and protect chromosomes from DNA degradation and end-fusion which can lead to chromosomal breaks and recombination. In telomerase-negative cells, each time a cell divides, the telomeres become shorter. When the telomeres get too short, the cell can no longer divide and ultimately leads to cellular senescence and death.

Studies have shown that diseases involving oxidative stress, inflammation and increased cell renewal are additional environmental factors that can accelerate telomere shortening and, at least in part, accelerate physiopathological processes. These diseases include, but are not limited to, autoimmune and immune-mediated diseases, inflammation diseases, chronic pulmonary diseases, such as, for example, chronic obstructive pulmonary disease (COPD) and idiopathic pulmonary fibrosis (IPF), atherosclerosis, and Duchenne muscular dystrophy (DMD).

Autoimmune and immune-mediated diseases include, for example, systemic lupus erythematosus, rheumatoid arthritis, Wegener's granulomatosis, sarcoidosis, systemic sclerosis, juvenile idiopathic arthritis, adult-onset still disease, myositis, psoriasis, atopic dermatitis, primary biliary cirrhosis, and autoimmune diabetes.

Chronic obstructive pulmonary disease (COPD), which encompasses diseases such as, for example, cystic fibrosis, chronic bronchitis, and emphysema, are steadily increasing in frequency, possibly due to continued smoking, increasing air pollution, and the continued aging of the population. For example, it has been estimated that in the United States alone, cystic fibrosis, a genetic disease, occurs in 1 out of every 2500 births, that 8 million people suffer from chronic bronchitis, and that 2 million individuals have emphysema. The number of deaths from these conditions, from both chronic disease complications and acute attacks, are continuing to increase. Moreover, deaths from just chronic obstructive pulmonary disease rose from 33,000 in 1970 to 62,000 in 1983.

IPF, which is one of about 200 diseases called interstitial lung diseases (ILDs), is a chronic, ultimately fatal disease characterized by a progressive decline in lung function. IPF usually occurs in adult individuals of between 50 and 70 years of age, particularly those with a history of cigarette smoking, affecting more men than women. IPF affects about 128,100 people in the United States, with about 48,000 newly diagnosed cases and 40,000 deaths annually.

Therefore, there remains a need for methods and compositions that overcome these deficiencies and that effectively treat short telomere disorders.

SUMMARY

In accordance with the purpose(s) of the invention, as embodied and broadly described herein, the invention, in one aspect, relates to methods of treating short telomere disorders using known compounds and pharmaceutical compositions comprising same.

Disclosed are methods for treating short telomere disorders, the method comprising the step of administering to the subject an effective amount of at least one lithium compound or a pharmaceutically acceptable salt thereof, thereby treating the subject for the short telomere disorder.

Also disclosed are methods for the treatment of a subject, the method comprising the steps of: diagnosing the subject as having a short telomere disorder; and administering to the subject an effective amount of at least one lithium compound or a pharmaceutically acceptable salt thereof.

Also disclosed are pharmaceutical compositions comprising an effective amount of at least one lithium compound or a pharmaceutically acceptable salt thereof; and an effective amount of at least one compound selected from: an agent known to treat an infection or a pharmaceutically acceptable salt thereof; and an agent known to modulate the immune system or pharmaceutically acceptable salt thereof, and an agent known to modulate the pulmonary system or pharmaceutically acceptable salt thereof; and a pharmaceutically acceptable carrier.

Also disclosed are kits comprising an effective amount of at least one lithium compound or a pharmaceutically acceptable salt thereof, and one or more of: at least one agent known to treat a short telomere disorder; at least one agent known to treat an immune-mediated disorder; at least one agent known to treat a pulmonary disorder; instructions for treating the short telomere disorder; instructions for treating the autoimmune disorder; instructions for treating the pulmonary disorder; or instructions for administering the lithium compound in connection with the short telomere disorder.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In some aspects of the disclosed methods, the subject has been diagnosed with a need for treatment of one or more short telomere associated disorder prior to the administering step. In some aspects of the disclosed method, the subject has been diagnosed with a chronic pulmonary disease prior to the administering step. In some aspects of the disclosed method, the subject been diagnosed with an chronic pulmonary disease prior to the administering step.

As used herein, the term "treatment" or "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a short telomere disorder prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "short telomere disorder" refer to a disease or disorder characterized by or exhibiting a telomere dysfunction. In further various aspects, the dysfunction is telomere shortening. In further various aspects, a short telomere disorder can comprise an immune-mediated disorder, inflammatory disorder, or chronic pulmonary disorder, such as, for example, idiopathic pulmonary fibrosis.

As used herein, "IC$_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an IC$_{50}$ can refer to the concentration of a substance that is required for 50% inhibition in vivo, as further defined elsewhere herein. In a further aspect, IC$_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein may comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., Almarasson, O., et. al. (2004) *The Royal Society of Chemistry*, 1889-1896. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds repurposed for use as agents for the treatment of short telomere disorders. More specifically, in one aspect, the present invention relates to compounds repurposed for the treatment of immune-mediated disorders, inflammatory disorders, chronic pulmonary disorders, and Duchenne muscular dystrophy (DMD).

It is contemplated that each disclosed derivative can be optionally further substituted. It is also contemplated that any one or more derivative can be optionally omitted from the invention. It is understood that the disclosed compounds can be employed in the disclosed methods of using.

In one aspect, the invention relates to lithium compounds or a pharmaceutically acceptable salt thereof. In a further aspect, the lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof. In a still further aspect, the lithium compound, or a pharmaceutically acceptable salt thereof is selected from lithium chloride, lithium bromide, lithium carbonate, lithium citrate, and lithium orotate.

In one further aspect, the lithium compound, or a pharmaceutically acceptable salt thereof is lithium chloride. In a further aspect, the lithium compound, or a pharmaceutically acceptable salt thereof is lithium bromide. In a still further aspect, the lithium compound, or a pharmaceutically acceptable salt thereof is lithium carbonate. In a yet further aspect, the lithium compound, or a pharmaceutically acceptable salt thereof is lithium citrate. In an even further aspect, the lithium compound, or a pharmaceutically acceptable salt thereof is lithium orotate.

C. METHODS FOR SHORT TELOMERE DISORDERS

In one aspect, the invention relates to methods for treating a short telomere disorder, the method comprising the step of administering to the subject an effective amount of at least one lithium compound or a pharmaceutically acceptable salt thereof, thereby treating the subject for the short telomere disorder.

In a further aspect, the short telomere disorder comprises a telomere dysfunction. In a still further aspect, the dysfunction is telomere shortening. In an even further aspect, the dysfunction is decreased cell signaling resulting in telomere shortening.

In a further aspect, the short telomere disorder is selected from immune-mediated disorder, inflammatory disorder, chronic pulmonary disorder, and Duchenne muscular dystrophy (DMD).

In a further aspect, the chronic pulmonary disorder is selected from interstitial lung diseases (ILD), idiopathic pulmonary fibrosis (IPF), chronic obstructive pulmonary disease (COPD), chronic bronchitis, and emphysema.

In a further aspect, immune-mediated disorder is selected from systemic lupus erythematosus, rheumatoid arthritis, Wegener's granulomatosis, sarcoidosis, systemic sclerosis, juvenile idiopathic arthritis, adult-onset still disease, myositis, psoriasis, atopic dermatitis, primary biliary cirrhosis, and autoimmune diabetes.

In one aspect, the short telomere disorder is Duchenne muscular dystrophy (DMD). In another aspect, the short telomere disorder is idiopathic pulmonary fibrosis (IPF). In yet another aspect, the short telomere disorder is chronic obstructive pulmonary disease (COPD).

To treat or control the short telomere disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a short telomere disorder, such as idiopathic pulmonary fibrosis (IPF).

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or condition.

The therapeutically effective amount or dosage of the compound can vary within wide limits Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In a further aspect, the subject is a mammal. In an even further aspect, the mammal is a human.

In a further aspect, the subject has been diagnosed with a need for treatment of the short telomere disorder prior to the administering step.

In a further aspect, wherein the subject has been diagnosed with a telomere dysfunction prior to the administering step. In a yet further aspect, the dysfunction is telomere shortening. In an even further aspect, the dysfunction is decreased cell signaling resulting in telomere shortening.

In a further aspect, the effective amount is a therapeutically effective amount. In a still further aspect, the effective amount is a prophylactically effective amount.

In a further aspect, the method further comprises the step of identifying a subject in need of treatment of the short telomere disorder.

In another aspect, the invention relates to a method for the treatment of a subject, the method comprising the steps of: a) diagnosing the subject as having a short telomere disorder; and b) administering to the subject an effective amount of at least one lithium compound or a pharmaceutically acceptable salt thereof.

In one aspect, a method of diagnosis of a short telomere disorder comprises performing an experiment upon the subject and identifying a level of a biological marker. In a further aspect diagnosing comprises determining, in a patient, levels of a marker (e.g., gene expression) indicative of a state of the patient, the state being predictive as to whether the patient will manifest reduced symptoms in response to a treatment.

In a further aspect, the biological marker is telomere length. In a still further aspect, the subject is a biological sample. In a still further aspect, the biological sample is selected from a cell, blood, saliva, urine, tissue, or phlegm. In an even further aspect, the experiment comprises the use of at least one of qPCR, FISH, NGS, and microarray. In other aspects, diagnosing comprises the use of an Ashcroft score.

In one aspect, diagnosis of a short telomere disorder comprises a medical history. In a further aspect, the diagnosis comprises comparing the findings of the medical history with the diagnostic standards. In a still further aspect, the diagnosis comprises finding of a telomere dysfunction.

In a yet further aspect, the dysfunction is telomere shortening. In an even further aspect, the dysfunction is decreased cell signaling resulting in telomere shortening.

D. PHARMACEUTICAL COMPOSITIONS

In one aspect, the invention relates to pharmaceutical compositions comprising an effective amount of at least one lithium compound or a pharmaceutically acceptable salt thereof; and an effective amount of at least one compound selected from: a) an agent known to treat an infection or a pharmaceutically acceptable salt thereof; and b) an agent known to modulate the immune system or pharmaceutically acceptable salt thereof, and c) an agent known to modulate the pulmonary system or pharmaceutically acceptable salt thereof; and a pharmaceutically acceptable carrier.

The compounds are active against short telomere disorders, and generally have $IC_{50}$ values ranging from about 0.01 micromolar to about 100 millimolar. $IC_{50}$ refers to the concentration of the compound that is required for 50% antagonism or inhibition of the target in vitro. $IC_{50}$ also refers to the concentration of a substance that is required for 50% antagonism or inhibition of the target in vivo. The activity of the compounds, including $IC_{50}$, is determined according to the procedures discussed below in the Examples section.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., Ansel, H. et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the effective amount is a therapeutically effective amount. In a still further aspect, the effective amount is a prophylactically effective amount.

In a further aspect, the composition is formulated for parenteral administration. In a still further aspect, the composition is formulated for inhalation. In yet a further aspect, the composition is formulated for oral administration. In an even further aspect, the composition is formulated for topical administration.

In a further aspect, the agent known to treat an infection is an antiviral or antibiotic. In a still further aspect, the antiviral can comprise oseltamivir, zanamavir, amantidine, rimantadine, ribavirin, gancyclovir, valgancyclovir, foscavir, Cytogam® (Cytomegalovirus Immune Globulin), pleconaril, rupintrivir, palivizumab, motavizumab, cytarabine, docosanol, denotivir, cidofovir, or acyclovir. In a yet further aspect, the antibiotic can comprise a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), or tuberculosis-mycobacterium antibiotics.

In a further aspect, the agent known to modulate the immune system is selected from a corticosteroid, a TNF inhibitor, an immunosuppressant, and a monoclonal antibody. In a still further aspect, the corticosteroid is selected from budesonide, cortisone, dexamethasone, hydrocortisone, methylprednisolone, prednisolone, prednisone, triamcinolone, beclomethasone, budesonide, ciclesonide, flunisolide, fluticasone, mometasone, and triamcinolone. In yet a further aspect, the TNF inhibitor is selected from adalimumab, certolizumab, etanercept, golimumab, and infliximab. In an even further aspect, the immunosuppressant is selected from cyclosporine, azathioprine, basiliximab, aclizumab, muromonab, tacrolimus, glatiramer acetate, mycopehnolate, and sirolimus.

In a further aspect, the agent known to modulate the immune system include compounds that inhibit/decrease cell signaling by inflammatory molecules like cytokines (e.g., IL-1, IL-4, IL-5, IL-6, IL-9, IL-13, IL-18 IL-25, IFN-a, IFN-β, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), growth factors (e.g., GM-CSF, NGF, SCF, TGF-β, EGF, VEGF and others) and/or their respective receptors. In a still further aspect, the agent known to modulate the immune system is selected from ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, Glaxo SmithKline PLC), CNT0148 (TNFa, Centocor, Inc, Johnson & Johnson, Schering-Plough Corp); Canakinumab (IL-Iβ, Novartis); Israpafant MITSUBISHI (PAF/IL-5, Mitsubishi Tanabe Pharma Corporation); IL-4 and IL-4 receptor antagonists/inhibitors: AMG317 (Amgen Inc), BAY 169996 (Bayer AG), AER-003 (Aerovance), APG-201 (Apogenix); IL-5 and IL-5 receptor antagonists/inhibitors: MEDI563 (AstraZeneca PLC, Medimmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, Medimmune, Inc); IL-13 and IL-13 receptor antagonists/inhibitors: TNX650 GENENTECH (Genentech), CAT-3M (AstraZeneca PLC, Medimmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (Glaxo SmithKline, Domantis), Pitrakinra/AEROO1/Aerovant™ (Aerovance Inc), AMG-317 (Amgen).

In a further aspect, the agent known to modulate the pulmonary system is selected from a mucoactive or mucolytic agent, surfactant, antihistamine, cough suppressant, bronchodilator, anti-inflammatory agent, steroid, and expectorant.

In a further aspect, the mucoactive or mucolytic agent is selected from MUCSAC and MUCSB mucins, DNA-ase, N-acetylcysteine (NAC), cysteine, nacystelyn, dornase alfa, gelsolin, heparin, heparin sulfate, P2Y2 agonists (e.g., UTP, INS365), nedocromil sodium, hypertonic saline, and mannitol. In a still further aspect, the surfactant is selected from L-alpha-phosphatidylcholine dipalmitoyl (DPPC), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars. In a yet further aspect, the antihistamine is selected from $H_1$-receptor antagonists (e.g., cetirazine, clemastine, asalastine, loratadine, and fexofenadine) and $H_2$-receptor antagonists (e.g., cimetidine, famotidine, lafutidine, nizatidine, ranitidine, roxatidine, and tiotidine). In an even further aspect, the cough suppressant is selected from benzonatate, benproperine, clobutinal, diphenhydramine, dextromethorphan, dibunate, fedrilate, glaucine, oxalamine, piperidione, and opiods (e.g., codeine). In a still further aspect, the bronchodilators is selected from short-acting beta-2 agonists (e.g., albuterol, epinephrine, pirbuterol, and levalbuterol), long-acting beta-2 agonists (LABA) (e.g., salmeterol, formoterol and isomers (e.g. arformoterol), clenbuterol, tulobuterol, vilanterol, indacaterol, carmoterol, isoproterenol, procaterol, bambuterol, milveterol, and olodaterol), long-acting muscarinic anagonists (LAMA) (e.g., tiotroprium, trospium chloride, glycopyrrolate, aclidinium, and ipratropium), combinations of LABAs and LAMAs, methylxanthines (e.g., aminophylline, ephedrine, theophylline, and oxtriphylline), short-acting anticholinergic agents (also referred to as short acting antimuscarinic) (e.g., ipratropium bromide and oxitropium bromide), and long-acting bronchodilators. In a yet further aspect, the anti-inflammatory agent is selected from leukotriene inhibitors and phosphodiesterase 4 (PDE4) inhibitors. In an even further aspect, the steroid is selected from budesonide, fluticasone, flunisolide, triamcinolone, beclomethasone, mometasone, ciclesonide, and dexamethasone.

It is understood that the disclosed compositions can be prepared from the disclosed compounds. It is also understood that the disclosed compositions can be employed in the disclosed methods of using.

E. KITS

In one aspect, the invention relates to a kit comprising an effective amount of at least one lithium compound or a pharmaceutically acceptable salt thereof, and one or more of: a) at least one agent known to treat a short telomere disorder; b) at least one agent known to treat an immune-mediated disorder; c) at least one agent known to treat a pulmonary disorder; d) instructions for treating the short telomere disorder; e) instructions for treating the autoimmune disorder; instructions for treating the pulmonary disorder; or g) instructions for administering the lithium compound in connection with the short telomere disorder.

The kits can also comprise compounds co-packaged, co-formulated, and/or co-delivered with other components. For example, a drug manufacturer, a drug reseller, a physician, a compounding shop, or a pharmacist can provide a kit comprising a disclosed compound and another component for delivery to a patient.

In a further aspect, the compound and the at least one agent are co-packaged. In a still further aspect, the compound and the at least one agent are co-formulated.

In a further aspect, the short telomere disorder is selected from immune-mediated disorder, inflammatory disorder, chronic pulmonary disorder, and Duchenne muscular dystrophy (DMD).

In a further aspect, the immune-mediated disorder is selected from systemic lupus erythematosus, rheumatoid arthritis, Wegener's granulomatosis, sarcoidosis, systemic sclerosis, juvenile idiopathic arthritis, adult-onset still disease, myositis, psoriasis, atopic dermatitis, primary biliary cirrhosis, and autoimmune diabetes.

In a further aspect, the pulmonary disorder is selected from idiopathic pulmonary fibrosis (IPF), chronic obstructive pulmonary disease (COPD), chronic bronchitis, and emphysema.

In a further aspect, the kit further comprises a plurality of dosage forms, the plurality comprising one or more doses; wherein each dose comprises an effective amount of the compound and the at least one agent. In a still further aspect, the effective amount is a therapeutically effective amount. In yet a further aspect, the effective amount is a prophylactically effective amount.

In a further aspect, each dose of the compound and the at least one agent are co-formulated. In a still further aspect, each dose of the compound and the at least one agent are co-packaged.

In a further aspect, each dose of the compound and the at least one agent are administered sequentially. In a still further aspect, each dose of the compound and the at least one agent are administered simultaneously.

In a further aspect, the dosage forms are formulated for oral administration, inhalation, topical administration, and/or parenteral administration. In a still further aspect, the dosage form for the compound is formulated for oral administration and the dosage form for the at least one agent is formulated for parental administration. In yet a further aspect, the dosage form for the compound is formulated for parental administration and the dosage form for the at least one agent is formulated for oral administration. In an even further aspect, the dosage form for the compound is formulated for topical administration and the dosage form for the at least one agent is formulated for parental administration. In a still further aspect, the dosage form for the compound is formulated for parental administration and the dosage form for the at least one agent is formulated for topical administration. In yet a further aspect, the dosage form for the compound is formulated for oral administration and the dosage form for the at least one agent is formulated for inhalation. In an even further aspect, the dosage form for the compound is formulated for inhalation and the dosage form for the at least one agent is formulated for oral administration. In a still further aspect, the dosage form for the compound is formulated for topical administration and the dosage form for the at least one agent is formulated for inhalation. In yet a further aspect, the dosage form for the compound is formulated for inhalation and the dosage form for the at least one agent is formulated for topical administration. In even further aspect, the dosage form for the lithium compound is formulated for oral administration and the dosage form for the at least one agent is formulated for oral administration. In still further aspect, the dosage form for the lithium compound is formulated for topical administration and the dosage form for the at least one agent is formulated for parenteral administration. In a yet further aspect, the dosage form for the lithium compound is formulated for topical administration and the dosage form for the at least one agent is formulated for topical administration. In a still further aspect, the dosage form for the lithium compound is formulated for inhalation administration and the dosage form for the at least one agent is formulated for inhalation. In a yet further aspect, the dosage form for the compound is formulated for inhalation administration and the dosage form for the at least one agent is formulated for oral administration.

It is understood that the disclosed kits can be prepared from the disclosed compounds, products, and pharmaceutical compositions. It is also understood that the disclosed kits can be employed in connection with the disclosed methods of using.

The disclosed devices and methods include at least the following aspects:

Aspect 1: A method for treating a short telomere disorder, the method comprising the step of administering to the subject an effective amount of at least one lithium compound or a pharmaceutically acceptable salt thereof, thereby treating the subject for the short telomere disorder.

Aspect: 2: The method of aspect 1, wherein the least one lithium compound, or a pharmaceutically acceptable salt thereof is selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof.

Aspect: 3: The method of aspect 2, wherein the least one lithium compound, or a pharmaceutically acceptable salt thereof is selected from lithium chloride, lithium bromide, lithium carbonate, lithium citrate, and lithium orotate.

Aspect: 4: The method of aspect 1, wherein the short telomere disorder is selected from an immune-mediated disorder, inflammatory disorder, chronic pulmonary disorder, and Duchenne muscular dystrophy (DMD).

Aspect: 5: The method of aspect 4, wherein the chronic pulmonary disorder is selected from interstitial lung diseases (ILD), idiopathic pulmonary fibrosis (IPF), chronic obstructive pulmonary disease (COPD), chronic bronchitis, and emphysema.

Aspect: 6: The method of aspect 4, wherein the immune-mediated disorder is selected from systemic lupus erythematosus, rheumatoid arthritis, Wegener's granulomatosis, sarcoidosis, systemic sclerosis, juvenile idiopathic arthritis, adult-onset still disease, myositis, psoriasis, atopic dermatitis, primary biliary cirrhosis, and autoimmune diabetes.

Aspect: 7: The method of aspect 1, wherein the short telomere disorder is Duchenne muscular dystrophy (DMD).

Aspect: 8: The method of aspect 1, wherein the short telomere disorder is idiopathic pulmonary fibrosis (IPF).

Aspect: 9: The method of aspect 1, wherein the short telomere disorder is chronic obstructive pulmonary disease (COPD).

Aspect: 10: The method of aspect 1, wherein the subject is a mammal.

Aspect: 11: The method of aspect 10, wherein the mammal is a human.

Aspect: 12: The method of aspect 1, wherein the subject has been diagnosed with a need for treatment of the short telomere disorder prior to the administering step.

Aspect: 13: The method of aspect 1, wherein the subject has been diagnosed with a telomere dysfunction prior to the administering step.

Aspect: 14: The method of aspect 13, wherein the dysfunction is decreased cell signaling resulting in telomere shortening.

Aspect: 15: The method of aspect 1, wherein the effective amount is a therapeutically effective amount.

Aspect: 16: The method of aspect 1, wherein the effective amount is a prophylactically effective amount.

Aspect: 17: The method of aspect 1, further comprising the step of identifying a subject in need of treatment of the short telomere disorder.

Aspect: 18: A method for the treatment of a subject comprising the steps of: (a) diagnosing the subject as having a short telomere disorder; and (b) administering to the subject an effective amount of at least one lithium compound or a pharmaceutically acceptable salt thereof.

Aspect: 19: The method of aspect 18, wherein diagnosing comprises performing an experiment upon the subject and identifying a level of a biological marker.

Aspect: 20: The method of aspect 18, wherein the biological marker is telomere length.

Aspect: 21: The method of aspect 18, where in the subject is a biological sample.

Aspect: 22: The method of aspect 18, where in the biological sample is selected from a cell, blood, saliva, urine, tissue, or phlegm.

Aspect: 23: The method of aspect 18, wherein the experiment comprises the use of at least one of qPCR, FISH, NGS, or microarray.

Aspect: 24: The method of aspect 18, wherein diagnosing comprises the use of Ashcroft score.

Aspect: 25: The method of aspect 18, wherein the short telomere disorder is selected from immune-mediated disorder, inflammatory disorder, chronic pulmonary disorder, and Duchenne muscular dystrophy (DMD).

Aspect: 26: The method of aspect 18, wherein the subject has been diagnosed with a telomere dysfunction prior to the administering step.

Aspect: 27: The method of aspect 26, wherein the dysfunction is decreased cell signaling resulting in telomere shortening.

Aspect: 28: A pharmaceutical composition comprising an effective amount of at least one lithium compound or a pharmaceutically acceptable salt thereof; and an effective amount of at least one compound selected from: (a) an agent known to treat an infection or a pharmaceutically acceptable salt thereof; and (b) an agent known to modulate the immune system or pharmaceutically acceptable salt thereof, and (c) an agent known to modulate the pulmonary system or pharmaceutically acceptable salt thereof; and a pharmaceutically acceptable carrier.

Aspect: 29: The composition of aspect 28, wherein the effective amount is a therapeutically effective amount.

Aspect: 30: The composition of aspect 28, wherein the effective amount is a prophylactically effective amount.

Aspect: 31: The composition of aspect 28, wherein the composition is formulated for inhalation administration.

Aspect: 32: The composition of aspect 28, wherein the composition is formulated for oral administration.

Aspect: 33: The composition of aspect 28, wherein the composition is formulated for topical administration.

Aspect: 34: The composition of aspect 28, wherein the agent known to treat an infection is selected from an antibiotic and an antiviral.

Aspect: 35: The composition of aspect 28, wherein the agent known to modulate the immune system is selected from a corticosteroid, a TNF inhibitor, an immunosuppressant, and a monoclonal antibody.

Aspect: 36: The composition of aspect 35, wherein the corticosteroid is selected from budesonide, cortisone, dexamethasone, hydrocortisone, methylprednisolone, prednisolone, prenisone, triamcinolone, beclomethasone, budesonide, ciclesonide, flunisolide, fluticasone, mometasone, and triamcinolone.

Aspect: 37: The composition of aspect 35, wherein the TNF inhibitor is selected from adalimumab, certolizumab, etanercept, golimumab, and infliximab.

Aspect: 38: The composition of aspect 35, wherein the immunosuppressant is selected from cyclosporine, azathioprine, basiliximab, aclizumab, muromonab, tacrolimus, glatiramer acetate, mycopehnolate, and sirolimus.

Aspect: 39: The composition of aspect 28, wherein the agent known to modulate the pulmonary system is selected from a mucoactive or mucolytic agent, surfactant, antihistamine, cough suppressant, bronchodilator, anti-inflammatory agent, steroid, and expectorant.

Aspect: 40: A kit comprising an effective amount of at least one lithium compound or a pharmaceutically acceptable salt thereof, and one or more of:
(a) at least one agent known to treat a short telomere disorder;
(b) at least one agent known to treat an immune-mediated disorder;
(c) at least one agent known to treat a pulmonary disorder;
(d) instructions for treating the short telomere disorder;
(e) instructions for treating the autoimmune disorder;
(f) instructions for treating the pulmonary disorder;
(g) instructions for administering the lithium compound in connection with the short telomere disorder.

Aspect: 41: The kit of aspect 40, wherein the lithium compound and the at least one agent are co-packaged.

Aspect: 42: The kit of aspect 40, wherein the lithium compound and the at least one agent are co-formulated.

Aspect: 43: The kit of aspect 40, wherein the short telomere disorder is selected from immune-mediated disorder, inflammatory disorder, chronic pulmonary disorder, and Duchenne muscular dystrophy (DMD).

Aspect: 44: The kit of aspect 40, wherein the immune-mediated disorder is selected from systemic lupus erythematosus, rheumatoid arthritis, Wegener's granulomatosis, sarcoidosis, systemic sclerosis, juvenile idiopathic arthritis, adult-onset still disease, myositis, psoriasis, atopic dermatitis, primary biliary cirrhosis, and autoimmune diabetes.

Aspect: 45: The kit of aspect 40, wherein the pulmonary disorder is selected from idiopathic pulmonary fibrosis (IPF), chronic obstructive pulmonary disease (COPD), chronic bronchitis, and emphysema.

Aspect: 46: The kit of aspect 40, further comprising a plurality of dosage forms, the plurality comprising one or more doses; wherein each dose comprises an effective amount of the compound and the at least one agent.

Aspect: 47: The kit of aspect 46, wherein the effective amount is a therapeutically effective amount.

Aspect: 48: The kit of aspect 46, wherein the effective amount is a prophylactically effective amount.

Aspect: 49: The kit of aspect 46, wherein each dose of the lithium compound and the at least one agent are co-formulated.

Aspect: 50: The kit of aspect 46, wherein each dose of the lithium compound and the at least one agent are co-packaged.

Aspect: 51: The kit of aspect 46, wherein each dose of the lithium compound and the at least one agent are administered sequentially.

Aspect: 52: The kit of aspect 46, wherein each dose of the lithium compound and the at least one agent are administered simultaneously.

Aspect: 53: The kit of aspect 46, wherein the dosage forms are formulated for oral administration, inhalation administration, topical administration, and/or parenteral administration.

Aspect: 54: The kit of aspect 46, wherein the dosage form for the lithium compound is formulated for oral administration and the dosage form for the at least one agent is formulated for parenteral administration.

Aspect: 55: The kit of aspect 46, wherein the dosage form for the lithium compound is formulated for oral administration and the dosage form for the at least one agent is formulated for oral administration.

Aspect: 56: The kit of aspect 46, wherein the dosage form for the lithium compound is formulated for topical administration and the dosage form for the at least one agent is formulated for parenteral administration.

Aspect: 57: The kit of aspect 46, wherein the dosage form for the lithium compound is formulated for topical administration and the dosage form for the at least one agent is formulated for topical administration.

Aspect: 58: The kit of aspect 46, wherein the dosage form for the lithium compound is formulated for inhalation administration and the dosage form for the at least one agent is formulated for inhalation.

Aspect: 59: The kit of aspect 46, wherein the dosage form for the compound is formulated for inhalation administration and the dosage form for the at least one agent is formulated for oral administration.

Aspect: 60: The kit of aspect 46, wherein the dosage form for the compound is formulated for inhalation administration and the dosage form for the at least one agent is formulated for parenteral administration.

Aspect: 61: The kit of aspect 46, wherein the dosage form for the compound is formulated for topical administration and the dosage form for the at least one agent is formulated for inhalation.

Aspect: 62: The kit of aspect 46, wherein the dosage form for the compound is formulated for inhalation administration and the dosage form for the at least one agent is formulated for topical administration.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. In Vivo Study: Lithium for Prevention of Pulmonary Fibrosis

In this Example, the effect of inhaled lithium carbonate on pulmonary fibrosis development was evaluated in mice receiving intra-tracheal bleomycin for bleomycin-induced pulmonary fibrosis. The general study methods of study was as follows:

Bleomycin solution: bleomycin (commercially available from SigmaAldrich) in PBS was used for intra-tracheal bleomycin administration. (0.04 U of bleomycin in 50 µl in PBS/mouse/per inhalation).

Lithium carbonate solution: (commercially available from SigmaAldrich) 0.15 mM Lithium carbonate solution in PBS was used for lithium administration.

13 female mice (commercially available from Charles River Laboratories, BALB/C) were randomly divided into 4 groups, as follows:

Group 1: No treatment (1 mice)
Group 2: Lithium inhalation treatment only (1 mice)
Group 3: Lithium inhalation treatment followed by bleomycin administration (6 mice)
Group 4: Bleomycin administration alone (5 mice)

The treatment protocol was as follows:

Each mouse was anesthetized with 87.5 mg ketamine/kg and 12.5 mg xyline/kg cocktail 0.1 ml/20 g body weight IM. For both lithium and bleomycin intra-tracheal administration, tracheal intubation was performed using with a 23 gauge IV catheter through the mouth, followed by insertion of PE-10 tubing into the trachea. After placement of the PE-10 tubing inside the trachea, the 23 gauge iv catheter was quickly removed. Lithium or bleomycin was instilled through the PE-10 tubing. The instillation volume was 50 µl each administration for each mouse. The procedure time was around 15 minutes per mouse.

For Group 1 (n=1), no treatment was administered and the mouse was sacrificed as control.

For Group 2 (n=1), intratracheal lithium was instilled every other day for 3 administrations (0.15 mM lithium carbonate in saline; volume 50 µl). The mice was sacrificed at 21 days after first lithium administration. The mice were sacrificed using pentobarbital 200 mg/kg ip. After the mice were sacrificed, the lungs were quickly harvested and perfused with 10% formalin buffer through the trachea. The lung tissue was then fixed in 10% formalin buffer for 3 days.

For Group 3 (n=6), the mice were pre-treated with intra-tracheal lithium instillation (0.15 mM in 50 µl saline) every other day for 3 administrations. 7 days after the final lithium pre-treatment, intra-tracheal bleomycin was instilled (0.04 U in 50 µl saline). The mice in this group were then sacrificed 14 days after bleomycin administration. The mice were sacrificed using pentobarbital 200 mg/kg ip. After the mice were sacrificed, the lungs were quickly harvested and perfused with 10% formalin buffer through the trachea. The lung tissue was then fixed in 10% formalin buffer for 3 days.

For Group 4 (n=5), only intra-tracheal bleomycin was instilled (0.04 U in 50 µl saline). The mice in this group were then sacrificed 14 days after bleomycin administration. The mice were sacrificed using pentobarbital 200 mg/kg ip. After the mice were sacrificed, the lungs were quickly harvested and perfused with 10% formalin buffer through the trachea. The lung tissue was then fixed in 10% formalin buffer for 3 days.

Following the 3 day period, macroscopical examination of the lung tissue was performed by dissection. The lung tissue were cut into 1-2 mm slices and visually inspected for areas of grey-white discoloration. The only areas of such discoloration were found in the lung tissue of Group 4 mice. The lung slices were then embedded in paraffin and sectioned into 5-µm-thick sections. Hematoxylin and eosin (H&E) and trichrome staining (abcam; ab150686) were performed for tissue samples from each group. The stained slides were then examined under light microscope (Olympus BX51) and photographed (Olympus DP-73 digital camera).

Figure 1A:
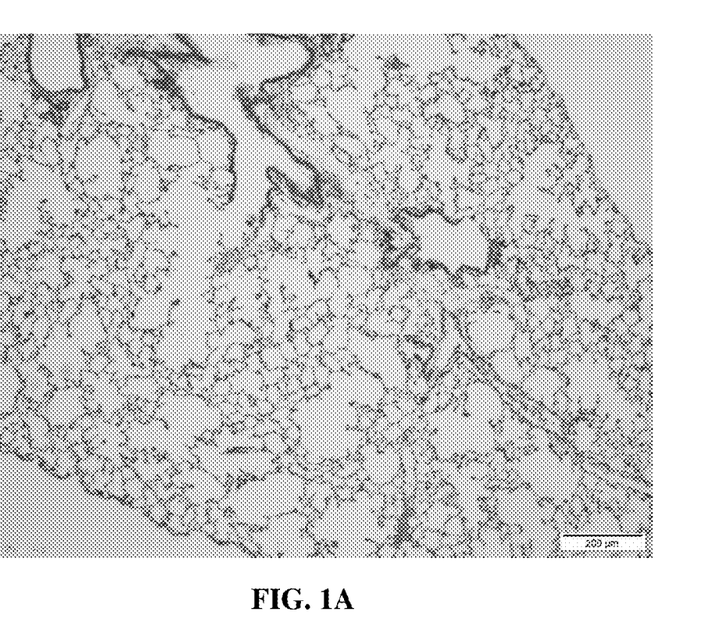
FIG. 1A and FIG. 1B show representative data pertaining to lung tissue samples from untreated mice.
Figure 1B:
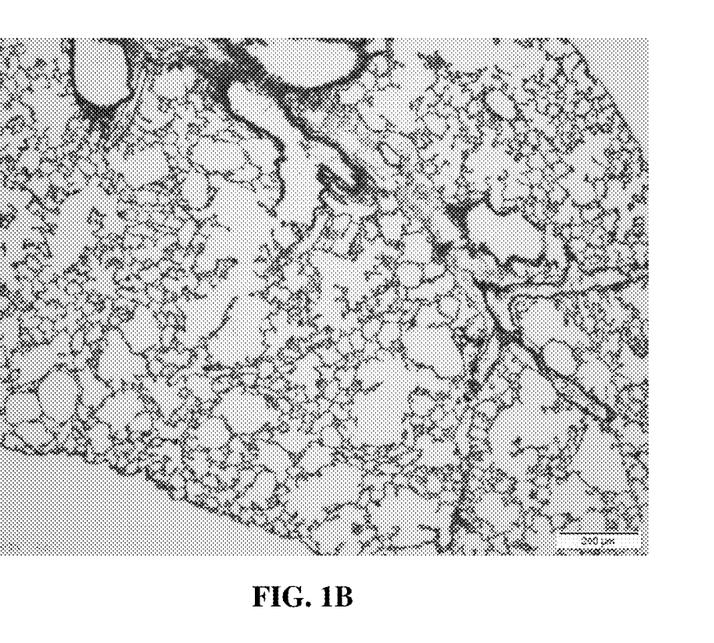
Figure 2A:
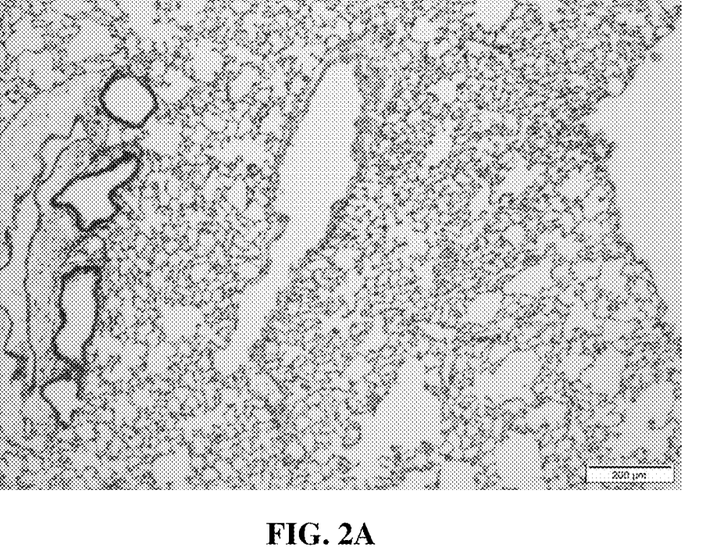
FIG. 2A and FIG. 2B show representative data pertaining to lung tissue samples from mice treated with lithium inhalation only.
Figure 2B:
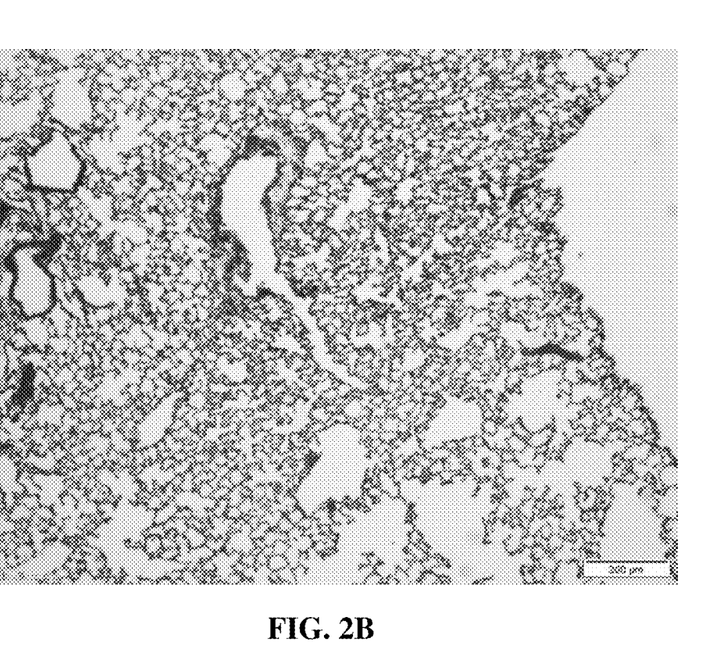

Results:

Group 1: Multiple section of the lungs were used as a standard of normal mice lungs macroscopically and microscopically. As shown in FIGS. 2A and 2B, no signs of lungs damage were seen.

Figure 3A:
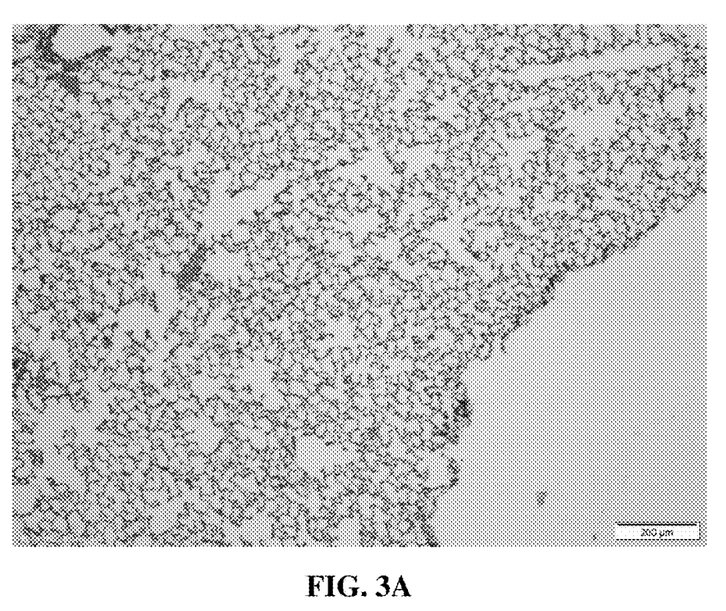
FIG. 3A and FIG. 3B show representative data pertaining to lung tissue samples from mice treated with lithium inhalation followed by bleomycin administration.
Figure 3B:
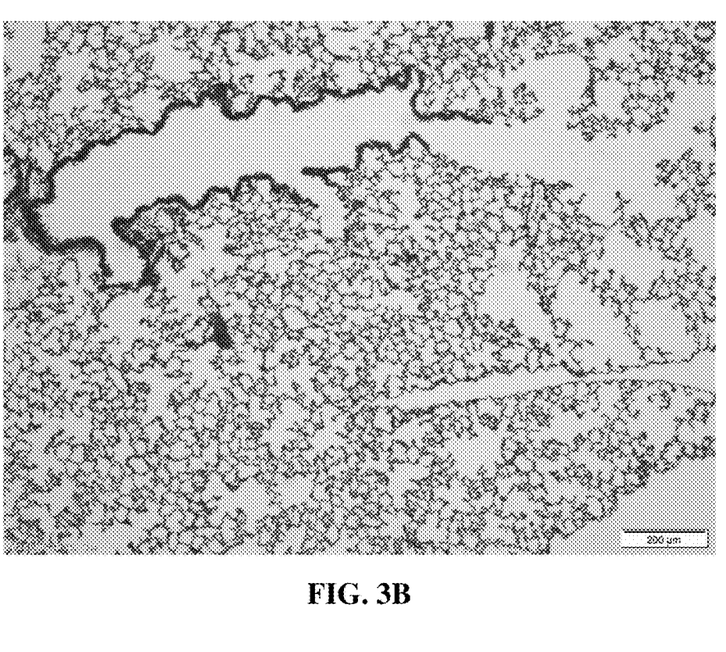

Group 2: As shown in FIGS. 3A and 3B, the tissue samples from Group 2 did not show any macroscopically or microscopically sign of lung tissue damage.

Figure 4A:
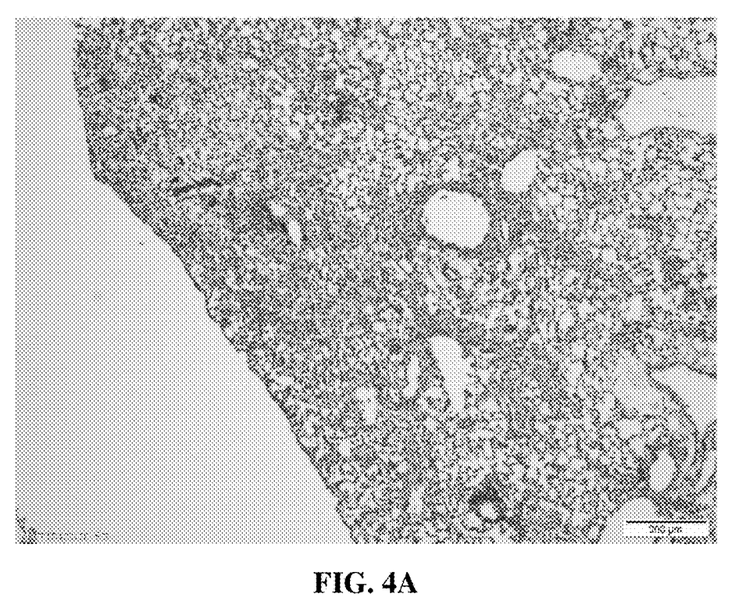
FIG. 4A-FIG. 4D show representative data pertaining to lung tissue samples from mice treated bleomycin only.
Figure 4B:
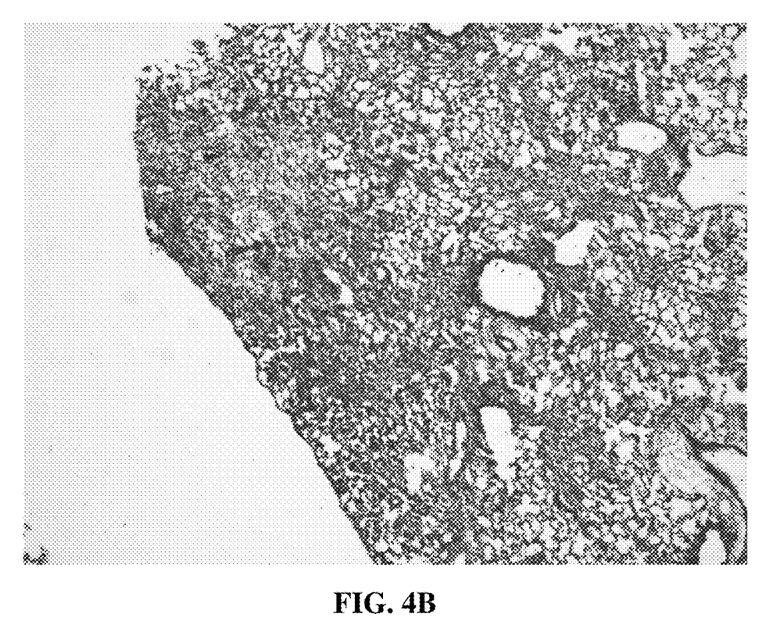
Figure 4C:
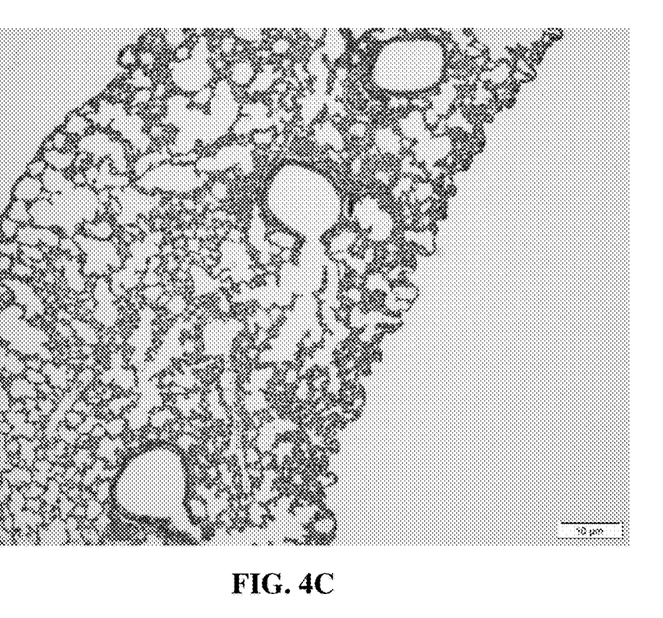
Figure 4D:
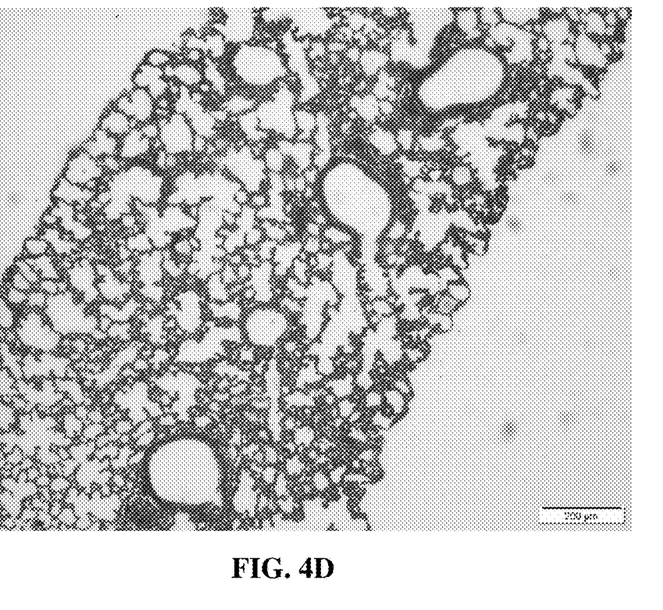

Group 3: As shown in FIGS. 4A and 4B, the lung sections from all 5 mice did not reveal any signs macroscopically or microscopically of lung tissue damage.

Group 4: As shown in FIGS. 5A-5D, the lung sections macroscopically revealed multiple areas of grey-white discoloration mostly in peri-pleural areas. These areas were confirmed to have profound fibrotic changes (FIGS. 5A-5b) or intense inflammation changes microscopically (FIGS. 5C-5D).

An Ashcroft score was then calculated for each of the group (T Ashcroft at al., Simple method of estimating severity of pulmonary fibrosis on a numerical scale. J Clin Pathol 1988; 41:467-470). The Ashcroft score provides a simple method of estimating severity of pulmonary fibrosis on a numerical scale.

The Ashcroft score for each of the group are as follows:
Group 1: (0)
Group 2: (0)
Group 3: (0)
Group 4: (4.03)

As the data suggests, lithium pre-treatment by inhalation completely abolishes pulmonary fibrosis development induced by bleomycin.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating idiopathic pulmonary fibrosis (IPF), the method comprising the step of administering to a subject an effective amount of at least one lithium compound selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof, or a pharmaceutically acceptable salt thereof, thereby treating the subject for idiopathic pulmonary fibrosis (IPF).

2. The method of claim 1, wherein the subject is a mammal.

3. The method of claim 1, wherein the subject has been diagnosed with a telomere dysfunction prior to the administering step.

4. The method of claim 3, wherein the dysfunction is decreased cell signaling resulting in telomere shortening.

5. The method of claim 1, wherein the effective amount is a therapeutically effective or prophylactically effective amount.

6. The method of claim 5, wherein the effective amount is a therapeutically effective amount.

7. The method of claim 1, further comprising the step of identifying a subject in need of treatment of idiopathic pulmonary fibrosis (IPF).

8. The method of claim 1, wherein administration is by inhalation.

9. A method for the treatment of a subject comprising the steps of:
   a. diagnosing the subject as having idiopathic pulmonary fibrosis (IPF); and
   b. administering to the subject an effective amount of at least one lithium compound selected from lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate, and combinations thereof, or a pharmaceutically acceptable salt thereof.

10. The method of claim 9, wherein diagnosing comprises performing an experiment upon the subject and identifying a level of a biological marker.

11. The method of claim 10, wherein the biological marker is telomere length.

12. The method of claim 11, wherein the subject has been diagnosed with a telomere dysfunction prior to the administering step.

13. The method of claim 12, wherein the dysfunction is decreased cell signaling resulting in telomere shortening.

14. The method of claim 9, wherein administration is by inhalation.

15. The method of claim 9, the effective amount is a therapeutically effective or prophylactically effective amount.

* * * * *